United States Patent
Inoue et al.

(10) Patent No.: US 11,767,308 B2
(45) Date of Patent: Sep. 26, 2023

(54) METHOD OF STABILIZING PERFLUORODIOXOLANE COMPOUND, PERFLUORODIOXOLANE COMPOUND-CONTAINING COMPOSITION AND METHOD OF PRODUCING PERFLUORODIOXOLANE COMPOUND POLYMER

(71) Applicants: TOSOH CORPORATION, Shunan (JP); TOSOH FINECHEM CORPORATION, Shunan (JP)

(72) Inventors: Daisuke Inoue, Shunan (JP); Yusuke Sesoko, Shunan (JP); Hiroshi Matsuo, Shunan (JP); Hiroki Takamiya, Shunan (JP); Hideyuki Mimura, Shunan (JP); Tomoya Shimono, Yokkaichi (JP); Tomonari Nagai, Yokkaichi (JP)

(73) Assignees: TOSOH CORPORATION, Shunan (JP); TOSOH FINECHEM CORPORATION, Shunan (JP)

( * ) Notice: Subject to any disclaimer, the term of this patent is extended or adjusted under 35 U.S.C. 154(b) by 0 days.

(21) Appl. No.: 17/788,901

(22) PCT Filed: Dec. 25, 2020

(86) PCT No.: PCT/JP2020/048947
§ 371 (c)(1),
(2) Date: Jun. 24, 2022

(87) PCT Pub. No.: WO2021/132640
PCT Pub. Date: Jul. 1, 2021

(65) Prior Publication Data
US 2023/0068345 A1 Mar. 2, 2023

(30) Foreign Application Priority Data
Dec. 26, 2019 (JP) .................. 2019-236416

(51) Int. Cl.
*C07D 317/42* (2006.01)
*C07C 50/04* (2006.01)
*C07C 50/12* (2006.01)

(52) U.S. Cl.
CPC .......... *C07D 317/42* (2013.01); *C07C 50/04* (2013.01); *C07C 50/12* (2013.01)

(58) Field of Classification Search
None
See application file for complete search history.

(56) References Cited

U.S. PATENT DOCUMENTS

| 2,737,533 A | 3/1956 | Marks et al. |
| 2019/0185600 A1 | 6/2019 | Saito et al. |

FOREIGN PATENT DOCUMENTS

| CN | 108912943 A | 11/2018 | |
| EP | 3 409 707 A1 | 12/2018 | |
| JP | 50-7046 B | 3/1975 | |
| JP | H05-107776 A * | 4/1993 | ............... G03G 5/02 |
| WO | WO 2018/062193 A1 | 4/2018 | |
| WO | WO 2020/130122 A1 | 6/2020 | |

OTHER PUBLICATIONS

International Search Report dated Feb. 16, 2021, in PCT/JP2020/048947 (with English Translation), 11 pages.
International Preliminary Report on Patentability and Written Opinion dated Jul. 7, 2022, in PCT/JP2020/048947 (with English Translation), 12 pages.
Yoshiyuki Okamoto et al., "New amorphous perfluoro polymers: perfluorodioxolane polymers for use as plastic optical fibers and gas separation membranes", Polym. Adv. Technol, 2016, 27, pp. 33-41.

* cited by examiner

*Primary Examiner* — Joseph R Kosack
(74) *Attorney, Agent, or Firm* — Oblon, McClelland, Maier & Neustadt, L.L.P.

(57) ABSTRACT

Provided is a method of stabilizing a perfluorodioxolane compound, which includes having a quinone compound present in a composition containing a perfluorodioxolane compound, wherein the perfluorodioxolane compound is one or more perfluorodioxolane compounds selected from the group consisting of a perfluorodioxolane compound denoted by general formula (1) and a perfluorodioxolane compound denoted by general formula (2).

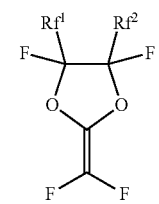

(1)

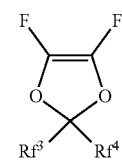

(2)

20 Claims, No Drawings

METHOD OF STABILIZING PERFLUORODIOXOLANE COMPOUND, PERFLUORODIOXOLANE COMPOUND-CONTAINING COMPOSITION AND METHOD OF PRODUCING PERFLUORODIOXOLANE COMPOUND POLYMER

CROSS-REFERENCE TO RELATED APPLICATIONS

The present application is a 35 U.S.C. § 371 national stage patent application of International patent application PCT/JP2020/048947, filed on Dec. 25, 2020, which is based on and claims the benefits of priority to Japanese Application No. 2019-236416, filed on Dec. 26, 2019. The entire contents of these applications are incorporated herein by reference.

TECHNICAL FIELD

The present invention relates to a method of stabilizing a perfluorodioxolane compound; a perfluorodioxolane compound-containing composition; and a method of producing a perfluorodioxolane compound polymer.

BACKGROUND ART

As a perfluorodioxolane compound, perfluoro(2-methylene-4-methyl-1,3-dioxolane) can be radically polymerized in the presence of an initiator, and can be used as a raw material for synthesizing poly[perfluoro(2-methylene-4-methyl-1,3-dioxolane)].

Poly[perfluoro(2-methylene-4-methyl-1,3-dioxolane)] is promising as a resin for gas separation membranes, a transparent resin for optical fibers, and the like. More specifically, poly[perfluoro(2-methylene-4-methyl-1,3-dioxolane)] is a transparent polymer having an amorphous structure, and has a high glass transition temperature (133 to 136° C.), and is expected to be used as a resin for next generation optical fibers and a resin for next generation gas separation membranes (see NPL 1).

On the other hand, addition of polymerization inhibitors such as a terpene-based compound disclosed in PTL 1 and a phenol-based compound disclosed in PTL 2 has been investigated in the past in order to stabilize fluorine-containing monomers during storage. In addition, PTL 3 discloses a 6-membered unsaturated cyclic hydrocarbon having a t-butyl group or the like as a polymerization inhibitor for a cyclic monomer that encompasses perfluoro(2-methylene-4-methyl-1,3-dioxolane).

[PTL 1] U.S. Pat. No. 2,737,533
[PTL 2] Japanese Examined Patent Publication No. S50-7046
[PTL 3] WO 2018/062193
[NPL 1] Y. Okamoto, et. al., Polym. Adv. Technol. 2016, 27, 33-41

SUMMARY OF INVENTION

In the applications mentioned, which are expected to be applications of poly[perfluoro(2-methylene-4-methyl-1,3-dioxolane)], it is essential to control molecular weight and polymer properties according to the purpose thereof. In order to achieve this, it is preferable to suppress polymerization reactions of the raw material perfluorodioxolane compound during storage and use this raw material in a polymerization reaction in a state whereby monomer quality is ensured. Furthermore, a high degree of quality stability, such as prevention of coloration, is also required in optical applications.

In addition, in the case of the polymerization inhibitor disclosed in PTL 3, distillation purification must be carried out in order to remove an unsaturated hydrocarbon used as the polymerization inhibitor in a case where a cyclic monomer is actually subjected to a polymerization reaction (see PTL 3: paragraph 0034 and the like) and thus the procedure is complicated. Furthermore, special equipment is essential for carrying out the polymerization In view of the circumstances mentioned above, one aspect of the present invention provides a novel means for stabilizing a perfluorodioxolane compound. More specifically, one aspect of the present invention provides a method of stabilizing a perfluorodioxolane compound, in which changes in quality, such as polymerization reactions and coloration during storage, are unlikely to occur, as well as a perfluorodioxolane compound polymerization reaction can be allowed to progress while a compound added in order to achieve stabilization can be separated in a simple manner or does not need to be separated.

As a result of diligent research into a perfluorodioxolane stabilization method, the present inventors newly found that by having a quinone compound having a specific structure present in a composition containing a perfluorodioxolane compound, changes in quality, such as polymerization reactions and coloration during storage, are unlikely to occur. Furthermore, the present inventors also found that because excellent stabilization is possible even if the quinone compound is present in an extremely small amount, a composition containing this quinone compound can be subjected to a polymerization reaction while the quinone compound can be separated in a simple manner or does not need to be separated.

One aspect of the present invention is as follows.

[1] A method of stabilizing a perfluorodioxolane compound (hereinafter also referred to simply as a "stabilization method"), which includes:

by having a quinone compound present in a composition containing a perfluorodioxolane compound, wherein the perfluorodioxolane compound is one or more perfluorodioxolane compounds selected from the group consisting of:

a perfluorodioxolane compound denoted by general formula (1) below:

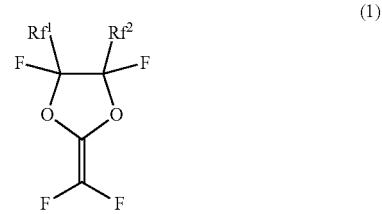

(In the formula, $Rf^1$ and $Rf^2$ each independently denote a fluorine atom or a perfluoroalkyl group having 1 to 6 carbon atoms, and an ether bond may be present in an arbitrary carbon-carbon bond in the perfluoroalkyl group. In addition, $Rf^1$ and $Rf^2$ may bond to each other to form a ring); and a perfluorodioxolane compound denoted by general formula (2) below:

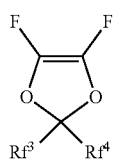

(2)

(In the formula, $Rf^3$ and $Rf^4$ each independently denote a fluorine atom or a perfluoroalkyl group having 1 to 6 carbon atoms, and an ether bond may be present in an arbitrary carbon-carbon bond in the perfluoroalkyl group); and the quinone compound is one or more quinone compounds selected from the group consisting of:

a quinone compound denoted by general formula (3) below:

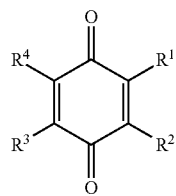

(3)

(In the formula, $R^1$ to $R^4$ each independently denote a hydrogen atom, a fluorine atom or a chlorine atom)

and a quinone compound denoted by general formula (4) below:

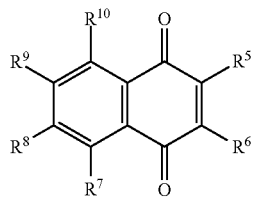

(4)

(In the formula, $R^5$ to $R^{10}$ each independently denote a hydrogen atom, a fluorine atom or a chlorine atom.)

[2] The method of stabilizing a perfluorodioxolane compound according to [1], wherein at least one of $R^1$ to $R^4$ in general formula (3) is a fluorine atom.

[3] The method of stabilizing a perfluorodioxolane compound according to [1] or [2], wherein the quinone compound includes the quinone compound denoted by general formula (3).

[4] The method of stabilizing a perfluorodioxolane compound according to any one of [1] to [3], wherein the quinone compound includes perfluoro-p-benzoquinone.

[5] The method of stabilizing a perfluorodioxolane compound according to any one of [1] to [4], wherein at least one of $R^5$ to $R^{10}$ in general formula (4) is a fluorine atom.

[6] The method of stabilizing a perfluorodioxolane compound according to any one of [1] to [5], wherein the quinone compound is present at a quantity of 0.1 to 500 ppm in terms of weight ratio relative to the perfluorodioxolane compound.

[7] The method of stabilizing a perfluorodioxolane compound according to [6], which further includes holding the composition, in which the quinone compound is present, in a container and using an inert gas atmosphere as an atmosphere of a gas phase part of the container.

[8] The method of stabilizing a perfluorodioxolane compound according to any one of [1] to [7], which further includes holding the composition, in which the quinone compound is present, at a temperature of 0° C. or lower.

[9] A perfluorodioxolane compound-containing composition which contains a perfluorodioxolane compound and a quinone compound, wherein the perfluorodioxolane compound is one or more perfluorodioxolane compounds selected from the group consisting of a perfluorodioxolane compound denoted by general formula (1) above and a perfluorodioxolane compound denoted by general formula (2) above, and the quinone compound is one or more quinone compounds selected from the group consisting of a quinone compound denoted by general formula (3) above and a quinone compound denoted by general formula (4) above.

[10] The perfluorodioxolane compound-containing composition according to [9], wherein the quinone compound is contained at a quantity of 0.1 to 500 ppm in terms of weight ratio relative to the perfluorodioxolane compound.

[11] The perfluorodioxolane compound-containing composition according to [9] or [10], wherein at least one of $R^1$ to $R^4$ in general formula (3) is a fluorine atom.

[12] The perfluorodioxolane compound-containing composition according to any one of [9] to [11], wherein the quinone compound includes the quinone compound denoted by general formula (3).

[13] The perfluorodioxolane compound-containing composition according to any one of [9] to [12], wherein the quinone compound includes perfluoro-p-benzoquinone.

[14] The perfluorodioxolane compound-containing composition according to any one of [9] to [13], wherein at least one of $R^5$ to $R^{10}$ in general formula (4) is a fluorine atom.

[15] A method of producing a perfluorodioxolane compound polymer, which includes adding a polymerization initiator to the perfluorodioxolane compound-containing composition according to any one of [9] to [14] to polymerize the perfluorodioxolane compound.

[16] A perfluorodioxolane compound-containing composition wherein a content of a perfluorodioxolane compound polymer is 1.0 weight % or less after the composition is stored under filling of nitrogen for 1 week or longer.

[17] A method of producing a perfluorodioxolane compound polymer which includes adding a polymerization initiator to the perfluorodioxolane compound-containing composition according to [16] to polymerize the perfluorodioxolane compound.

According to one aspect of the present invention, it is possible to provide a perfluorodioxolane compound-containing composition that is unlikely to undergo changes in quality, such as polymerization reactions and coloration, during storage.

DESCRIPTION OF EMBODIMENTS

[Stabilization Method]

One aspect of the present invention relates to a method of stabilizing a perfluorodioxolane compound by having a quinone compound present in a composition containing a perfluorodioxolane compound. The perfluorodioxolane compound is one or more perfluorodioxolane compounds selected from the group consisting of a perfluorodioxolane compound denoted by general formula (1) above and a perfluorodioxolane compound denoted by general formula (2) above, and the quinone compound is one or more quinone compounds selected from the group consisting of a quinone compound denoted by general formula (3) above and a quinone compound denoted by general formula (4) above.

According to the stabilization method described above, by having a quinone compound having a specific structure present in a composition containing a perfluorodioxolane compound, it is possible to suppress progress of polymerization reactions of the perfluorodioxolane compound during storage and also suppress coloration. The perfluorodioxolane compound may be a single component or a composition of two or more perfluorodioxolane compounds. In addition, the specific quinone compound may be a single component or a composition of two or more quinone compounds. More specifically, according to the stabilization method described above, by having one or more quinone compounds, selected from among a quinone compound denoted by general formula (3) and a quinone compound denoted by general formula (4), present in a composition containing the perfluorodioxolane compound, it is possible to suppress progress of polymerization reactions of the perfluorodioxolane compound during storage and also suppress coloration.

<Perfluorodioxolane Compound>

The perfluorodioxolane compound to be stabilized by the above stabilization method is selected from the group consisting of a perfluorodioxolane compound denoted by general formula (1) and a perfluorodioxolane compound denoted by general formula (2). Hereinafter, a perfluorodioxolane compound denoted by general formula (1) is referred to as "perfluorodioxolane compound A", and a perfluorodioxolane compound denoted by general formula (2) is referred to as "perfluorodioxolane compound B".

(Perfluorodioxolane Compound A)

Perfluorodioxolane compound A is denoted by general formula (1). In general formula (1), $Rf^1$ and $Rf^2$ each independently denote a fluorine atom or a perfluoroalkyl group having 1 to 6 carbon atoms, and an ether bond may be present in an arbitrary carbon-carbon bond in the perfluoroalkyl group. In addition, $Rf^1$ and $Rf^2$ may bond to each other to form a ring.

A perfluoroalkyl group having 1 to 6 carbon atoms, which is one embodiment of $Rf^1$ and $Rf^2$, may be straight chain or branched chain. Specific examples of the perfluoroalkyl group include a trifluoromethyl group, a pentafluoroethyl group, a heptafluoro-n-propyl group, a heptafluoro-isopropyl group, a nonafluoro-n-butyl group, a nonafluoro-isobutyl group, a nonafluoro-sec-butyl group, a nonafluoro-tert-butyl group, a perfluoro(methoxymethyl) group and a perfluoro(ethoxymethyl) group. Of these, a trifluoromethyl group, a pentafluoroethyl group and a perfluoro(methoxymethyl) group are preferred from the perspective of ease of production, and a trifluoromethyl group is more preferred.

It is particularly preferable for $Rf^1$ and $Rf^2$ in general formula (1) to be fluorine atoms or trifluoromethyl groups. In one embodiment, it is preferable for both $Rf^1$ and $Rf^2$ to be fluorine atoms. In another embodiment, it is preferable for both $Rf^1$ and $Rf^2$ to be trifluoromethyl groups.

The example compounds listed below can be given as examples of the perfluorodioxolane compound A. However, the present invention is not limited to these.

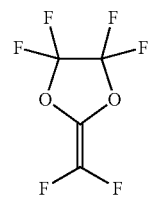

1-1

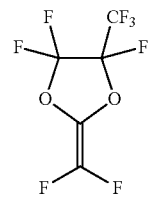

1-2

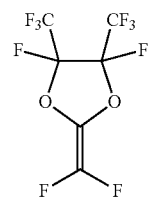

1-3

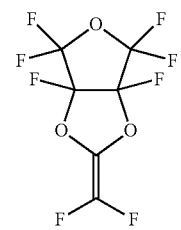

1-4

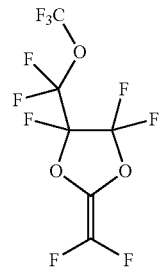

1-5

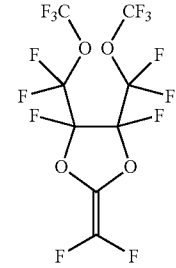

1-6

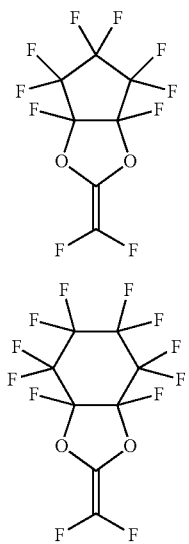

1-7

1-8

Example compound 1-2 is perfluoro(2-methylene-4-methyl-1,3-dioxolane). In the present invention, it is particularly preferable for the compound to be stabilized to be perfluoro(2-methylene-4-methyl-1,3-dioxolane).

Perfluorodioxolane compound A can be obtained using a method that is already known from literature, such as a method described in Macromolecules 2005, 38, 4237-4245 or U.S. Pat. No. 4,776,536.

(Perfluorodioxolane Compound B)

Perfluorodioxolane compound B is denoted by general formula (2). In general formula (2), $Rf^3$ and $Rf^4$ each independently denote a fluorine atom or a perfluoroalkyl group having 1 to 6 carbon atoms, and an ether bond may be present in an arbitrary carbon-carbon bond in the perfluoroalkyl group.

A perfluoroalkyl group having 1 to 6 carbon atoms, which is one embodiment of $Rf^3$ and $Rf^4$, may be straight chain or branched chain. Specific examples of the perfluoroalkyl group include a trifluoromethyl group, a pentafluoroethyl group, a heptafluoro-n-propyl group, a heptafluoro-isopropyl group, a nonafluoro-n-butyl group, a nonafluoro-isobutyl group, a nonafluoro-sec-butyl group, a nonafluoro-tert-butyl group, a perfluoro(methoxymethyl) group and a perfluoro(ethoxymethyl) group. Of these, a trifluoromethyl group, a pentafluoroethyl group and a perfluoro(methoxymethyl) group are preferred from the perspective of ease of production, and a trifluoromethyl group is more preferred.

It is particularly preferable for $Rf^3$ and $Rf^4$ in general formula (2) to be fluorine atoms or trifluoromethyl groups. In one embodiment, it is preferable for both $Rf^3$ and $Rf^4$ to be fluorine atoms. In another embodiment, it is preferable for both $Rf^3$ and $Rf^4$ to be trifluoromethyl groups.

Perfluorodioxolane compound B can be obtained using a method that is already known from literature, such as a method described in Macromolecules 1993, 26, 5829-5834.

In the stabilization method described above, the quinone compound is present in a composition containing the above perfluorodioxolane compound. The perfluorodioxolane compound contained in this composition can be a single compound in one embodiment or a combination of two or more compounds in another embodiment. For example, the above composition can contain one or more of perfluorodioxolane compound A only, one or more of perfluorodioxolane compound B only, or one or more of perfluorodioxolane compound A and one or more of perfluorodioxolane compound B. Two or more of perfluorodioxolane compound can be contained in the composition at an arbitrary mixing ratio.

<Quinone Compound>

Next, the quinone compound will be explained.

The quinone compound present in the perfluorodioxolane compound-containing composition is selected from the group consisting of a quinone compound denoted by general formula (3) and a quinone compound denoted by general formula (4). Hereinafter, a quinone compound denoted by general formula (3) is referred to as "quinone compound a" and a quinone compound denoted by general formula (4) is referred to as "quinone compound b".

(Quinone Compound a)

Quinone compound a is denoted by general formula (3). In general formula (3), $R^1$ to $R^4$ each independently denote a hydrogen atom, a fluorine atom or a chlorine atom.

It is preferable for at least one of $R^1$ to $R^4$ to be a fluorine atom or a chlorine atom, and it is more preferable for at least one of $R^1$ to $R^4$ to be a fluorine atom. In one embodiment, quinone compound a denoted by general formula (3) is preferably a perfluoro compound, that is, a compound in which all of $R^1$ to $R^4$ in general formula (3) are fluorine atoms.

The example compounds listed below can be given as examples of quinone compound a. However, the present invention is not limited to these.

3-1

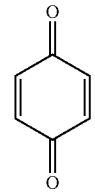

3-2

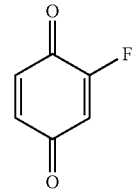

3-3

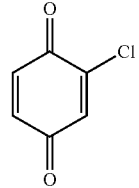

3-4

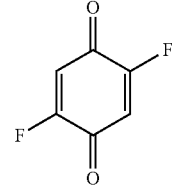

-continued 3-5
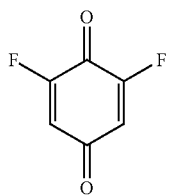

3-6
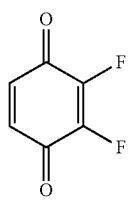

3-7
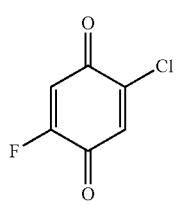

3-8
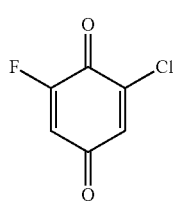

3-9
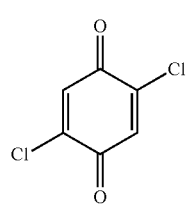

3-10
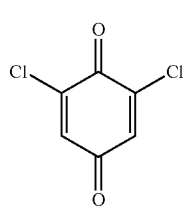

3-11
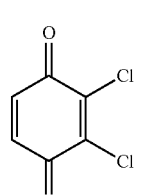

3-12
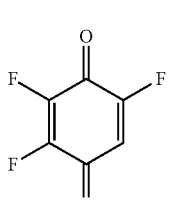

-continued 3-13
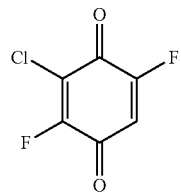

3-14
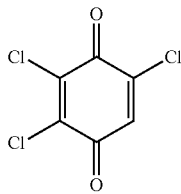

3-15
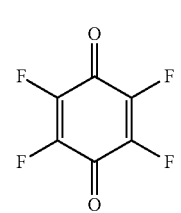

3-16
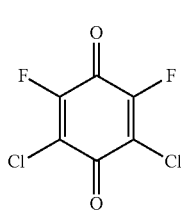

3-17
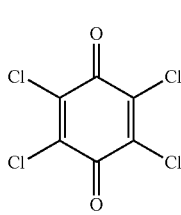

In general formula (3), it is more preferable for all of $R^1$ to $R^4$ to be fluorine atoms, that is, for quinone compound a to be perfluoro-p-benzoquinone (example compound 3-15), from the perspectives of suppressing coloration and suppressing polymerization.

It is particularly preferable for quinone compound a to be perfluoro-p-benzoquinone from the perspective of ease of procurement.

(Quinone Compound b)

Quinone compound b is denoted by general formula (4). In general formula (4), $R^5$ to $R^{10}$ each independently denote a hydrogen atom, a fluorine atom or a chlorine atom.

It is preferable for at least one of $R^5$ to $R^{10}$ to be a fluorine atom or a chlorine atom, and it is more preferable for at least one of $R^5$ to $R^{10}$ to be a fluorine atom. In one embodiment, quinone compound b denoted by general formula (4) is preferably a perfluoro compound, that is, a compound in which all of $R^5$ to $R^{10}$ in general formula (4) are fluorine atoms.

The example compounds listed below can be given as examples of quinone compound b. However, the present invention is not limited to these.

4-1 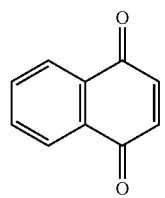
4-2 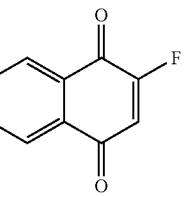
4-3 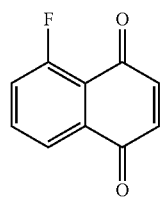
4-4 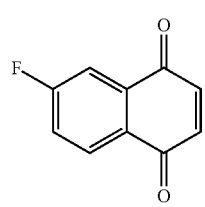
4-5 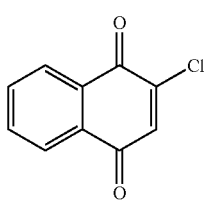
4-6 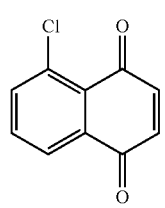
4-7 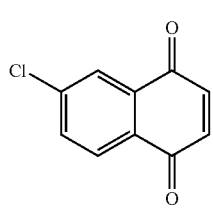
4-8 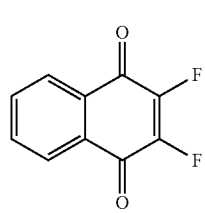
4-9 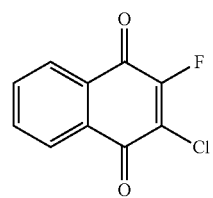
4-10 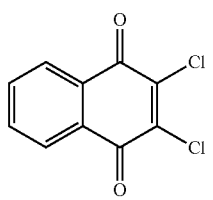
4-11 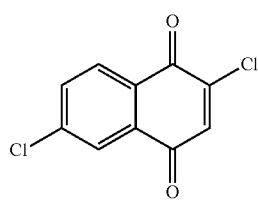
4-12 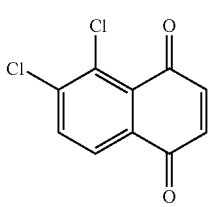
4-13 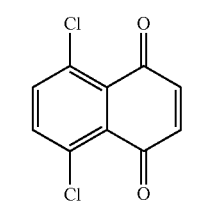
4-14 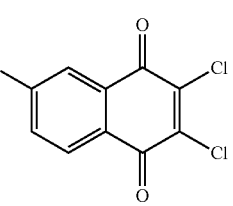
4-15 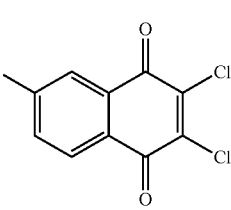
4-16 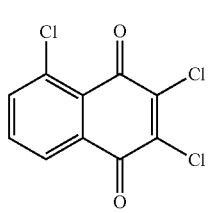

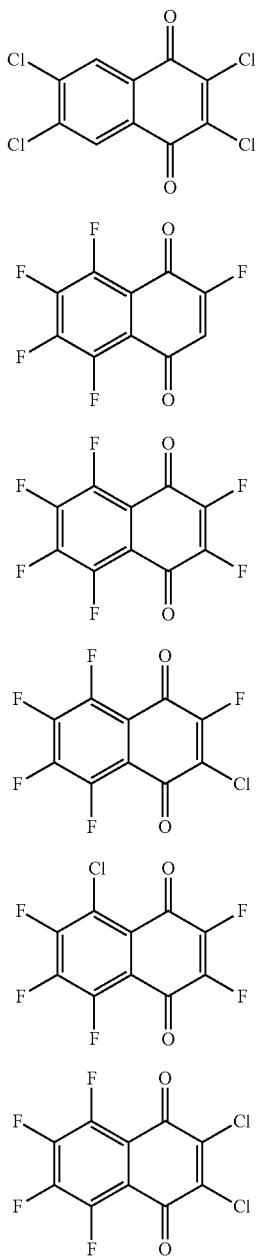

4-17

4-18

4-19

4-20

4-21

4-22

In general formula (4), it is more preferable for all of $R^5$ to $R^{10}$ to be fluorine atoms, that is, for quinone compound b to be perfluoro-p-naphthoquinone (example compound 4-19), from the perspectives of suppressing coloration and suppressing polymerization.

In the stabilization method described above, the quinone compound is present in the composition containing the above perfluorodioxolane compound. The quinone compound added to this composition can be a single compound in one embodiment or a combination of two or more compounds in another embodiment. For example, the above composition can contain one or more of quinone compound a only, one or more of quinone compound b only, or one or more of quinone compound a and one or more of quinone compound b. Two or more of quinone compound can be added to the above composition at an arbitrary mixing ratio.

In a case where two or more compounds are used, the content and added quantity refer to the total amount of these two or more compounds.

The quantity of quinone compound added to the above composition is, relative to the perfluorodioxolane compound in terms of weight ratio, preferably 0.01 to 500 ppm, more preferably 0.1 to 500 ppm, further preferably 0.5 to 100 ppm, further preferably 0.5 to 40 ppm, and further preferably 1 to 30 ppm.

Even if the above quinone compound is added at an extremely small quantity, it is possible to achieve a perfluorodioxolane compound stabilization effect, and a satisfactory stabilization effect can be achieved at an added quantity of 500 ppm or less. When carrying out a polymerization reaction, the added quantity of the quinone compound is preferably 500 ppm or less, more preferably 100 ppm or less, and further preferably 30 ppm or less, from the perspective of not requiring a quinone compound removal procedure or being able to easily remove the quinone compound. On the other hand, the added quantity of the quinone compound is preferably 0.1 ppm or more, more preferably 0.5 ppm or more, and further preferably 1 ppm or more, from the perspective of further increasing the stabilization effect. Hereinafter, ppm units for weight ratio are denoted as "ppm by weight".

In addition, the quantity of quinone compound added to the perfluorodioxolane compound is, in terms of weight ratio, preferably 0.01 to 4.0 ppm, and more preferably 0.05 to 2.0 ppm, from the perspective of using the quinone compound-containing composition to produce a polymer.

The above quinone compound may undergo sedimentation or phase separation without dissolving in the composition that contains the above perfluorodioxolane compound. It is preferable for the quinone compound to dissolve in the composition that contains the above perfluorodioxolane compound from the perspective of achieving a more uniform stabilization effect throughout the entire perfluorodioxolane compound contained in the composition during storage.

<Optional Components>

One or more other components can be contained in the composition that contains the above perfluorodioxolane compound and the quinone compound, and examples of components able to be optionally contained in the above composition include by-products generated in the process for synthesizing the perfluorodioxolane compound. Examples of such by-products include a 2-hydro-perfluorodioxolane compound denoted by general formula (5) below.

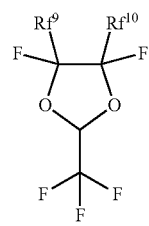

(5)

In the formula, $Rf^9$ and $Rf^{10}$ each independently denote a fluorine atom or a perfluoroalkyl group having 1 to 6 carbon atoms, and an ether bond may be present in an arbitrary carbon-carbon bond in the perfluoroalkyl group. In addition, $Rf^9$ and $Rf^{10}$ may bond to each other to form a ring. Details for $Rf^9$ and $Rf^{10}$ are as described above in relation to $Rf^1$ and $Rf^2$.

In some cases, the above composition might contain, for example, 2-hydro-perfluoro(2,4-dimethyl-1,3-dioxolane) having a structure denoted by formula (6) below, which is a by-product generated in the process for synthesizing perfluoro(2-methylene-4-methyl-1,3-dioxolane), as a 2-hydro-perfluorodioxolane compound denoted by general formula (5).

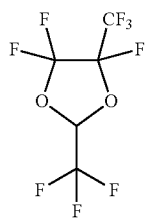
(6)

In general, the content of the above by-product is less than 10% in terms of weight ratio relative to the perfluorodioxolane compound.

In addition, the above composition may contain a solvent. The solvent is not particularly limited, but is preferably a solvent which can dissolve the perfluorodioxolane compound, does not react with the perfluorodioxolane compound, and does not impair a polymerization reaction in a subsequent step. Specific preferred examples of the solvent include: fluorine-containing solvents, such as fluorinated chain-like alkanes such as perfluorohexane, $C_6F_{13}C_2H_5$ and $C_2F_5CHFCHFCF_3$; fluorinated cyclic alkanes such as c-$C_5F_7H_3$; fluorinated aromatic compounds such as hexafluorobenzene, trifluoromethyibenzene and perfluorotoluene; fluoroalkyl ethers such as $CF_3CH_2OCF_2CF_2H$, $C_4F_9OCH_3$, $C_4F_9OC_2H_5$ and $C_6F_{13}OCH_{13}$; and fluorinated alkylamines such as perfluorotripropylamine and perfluorotributylamine. The content of the solvent is preferably 0.1 to 10 times the quantity of the perfluorodioxolane compound in terms of weight ratio.

<Container for Composition>

Examples of the container used for holding the composition during storage, transportation, and the like, include containers made of resins such as polyethylene, polypropylene and polytetrafluoroethylene; containers made of metals such as stainless steel; glass containers; and composite containers of resins and metals. Of these, resin containers and composite containers of resins and metals are preferred from perspectives such as corrosion resistance.

Components contained in the above composition can be introduced into the container either simultaneously or sequentially in an arbitrary order. In a case where a gas phase (that is, a space) is present in the container, it is preferable for the atmosphere of the gas phase of the container to be an inert gas atmosphere. Examples of inert gases include nitrogen, argon and carbon dioxide. By filling the gas phase of the container with an inert gas, it is possible to increase the stability of the perfluorodioxolane compound against oxidation and the like.

<Temperature of Composition>

The temperature of the above composition is preferably room temperature or lower, and it is more preferable to maintain a temperature of 0° C. or lower. By setting the temperature to be 0° C. or lower, a stabilization effect can be maintained for a long period of time, and it is possible to further increase the stabilization effect, such as suppressing temperature-dependent reactions, such as a dimerization reaction of the perfluorodioxolane compound. Room temperature can be taken to be, for example, approximately 25° C.

[Perfluorodioxolane Compound-Containing Composition]

In addition, one aspect of the present invention relates to a perfluorodioxolane compound-containing composition which contains a perfluorodioxolane compound and a quinone compound, wherein the perfluorodioxolane compound is one or more perfluorodioxolane compounds selected from the group consisting of a perfluorodioxolane compound denoted by general formula (1) above and a perfluorodioxolane compound denoted by general formula (2) above, and the quinone compound is one or more quinone compounds selected from the group consisting of a quinone compound denoted by general formula (3) above and a quinone compound denoted by general formula (4) above (hereinafter referred to as "composition 1"). Details of this composition are as described above.

In addition, one aspect of the present invention relates to a perfluorodioxolane compound-containing composition in which the content of a perfluorodioxolane compound polymer is 1.0 weight % or less after the composition is stored under filling of nitrogen for 1 week or longer (hereinafter referred to as "composition 2"). The above storage means storage at room temperature, and can mean storage in a storage environment at a temperature of 25° C., for example. In addition, the start of storage can be taken to be any point in time following completion of the preparation of the perfluorodioxolane compound-containing composition. The content of a perfluorodioxolane compound polymer in the above perfluorodioxolane compound-containing composition is preferably 1.0 weight % or less after the composition is stored under shielding of light and filling of nitrogen for 30 days at room temperature. Here, a perfluorodioxolane compound polymer after storage means a polymer that can be recovered as a solid residue after the above perfluorodioxolane compound-containing composition is dried or filtered after addition of a poor solvent. The content of the perfluorodioxolane compound polymer after storage can be, for example, 0.1 ppm by weight or more, and can be lower than this value. In one embodiment, it is preferable for no solid residue to be confirmed after storage.

In the present specification, matters described in composition 1 can also be applied to composition 2, and matters described in composition 2 can also be applied to composition 1.

[Method of Producing Perfluorodioxolane Compound Polymer]

In addition, one aspect of the present invention relates to a method of producing a perfluorodioxolane compound polymer (hereinafter referred to as "production method 1"), which includes adding a polymerization initiator to a perfluorodioxolane compound-containing composition to polymerize the perfluorodioxolane compound, wherein the above perfluorodioxolane compound-containing composition contains a perfluorodioxolane compound and a quinone compound, the above perfluorodioxolane compound is one or more perfluorodioxolane compounds selected from the group consisting of a perfluorodioxolane compound denoted by general formula (1) above and a perfluorodioxolane compound denoted by general formula (2) above, and the above quinone compound is one or more quinone compounds selected from the group consisting of a quinone compound denoted by general formula (3) above and a quinone compound denoted by general formula (4) above.

The production method described above can be a method including polymerizing the above composition after removing the quinone compound or a method including polymerizing the above composition without removing the quinone compound. The method, which includes polymerizing the composition containing the quinone compound, is preferred. That is because the polymer obtained can exhibit satisfactory transparency with no coloration even if the quinone compound is not removed, as well as a quinone compound removal step, such as purification by distillation, can be omitted.

At the time of polymerization, the above composition may contain other monomers. Examples of the other monomers include tetrafluoroethylene, trifluoroethylene, chlorotrifluoroethylene, vinylidene fluoride, vinyl fluoride, ethylene, propylene, methyl vinyl ether, ethyl vinyl ether, n-propyl vinyl ether, n-butyl vinyl ether, isopropyl vinyl ether, tert-butyl vinyl ether, 2-ethylhexyl vinyl ether, cyclohexyl vinyl ether, ethylene glycol vinyl ether, diethylene glycol divinyl ether, 1,4-butanediol vinyl ether, 1,4-butanediol divinyl ether, 1,4-cyclohexanedimethanol divinyl ether, 2-chloroethyl vinyl ether, perfluoro(methyl vinyl ether), perfluoro(ethyl vinyl ether), perfluoro(n-propyl vinyl ether), perfluoro(isopropyl vinyl ether), 2-(heptafluoropropoxy) hexafluoropropyl trifluorovinyl ether, perfluoro(3-butenyl vinyl ether), perfluoro(allyl vinyl ether), perfluoro-α-olefin (hexafluoropropylene) and the like), (perfluoroalkyl)ethylene (perfluorobutyl)ethylene and the like), (perfluoroalkyl) propene (3-perfluorooctyl-1-propene and the like), perfluoro (alkyl vinyl ether), and the like.

A polymerization method such as emulsion polymerization, solution polymerization, suspension polymerization or bulk polymerization can be used as the polymerization method. A solution polymerization method or suspension polymerization method is preferred as the polymerization method. In the case of solution polymerization, a monomer component is polymerized in a polymerization medium in a reaction vessel in the presence of a polymerization initiator to obtain a mixture containing a fluorine-containing polymer, unreacted cyclic monomer, the polymerization medium, initiator degradation products, and the like.

A solvent such as a chlorofluorocarbon, a hydrochlorofluorocarbon, a hydrofluorocarbon, a hydrofluoroether or 1,1,2,2,3,3,4-heptafluorocyclopentane is preferred as the polymerization medium, and a hydrofluorocarbon, a hydrofluoroether or 1,1,2,2,3,3,4-heptafluorocyclopentane, which have a low environmental burden, is more preferred.

Perfluorobenzoyl peroxide can be given as an example of the polymerization initiator. The usage quantity of the polymerization initiator is preferably 0.01 to 10 parts by mass relative to the total amount of monomer component.

The polymerization temperature is preferably from 0° C. to +100° C.

The polymerization duration is preferably 1 minute or more and 48 hours or less.

In addition, one aspect of the present invention relates to a method of producing a perfluorodioxolane compound polymer (hereinafter referred to as "production method 2"), which includes adding a polymerization initiator to the perfluorodioxolane compound-containing composition mentioned above to polymerize the perfluorodioxolane compound, in which the content of a perfluorodioxolane compound polymer is 1.0 weight % or less after the composition is stored under filling of nitrogen for 1 week or longer. The composition to which the polymerization initiator is to be added can be a composition after the above storage in one embodiment, and can be a composition which has not been subjected to the above storage in another embodiment.

In the present specification, matters described in production method 1 can also be applied to production method 2, and matters described in production method 2 can also be applied to production method 1.

EXAMPLES

The present invention will now be explained in greater detail through Examples below, but the present invention is not limited to Examples.

The following equipment was used for analysis.
GC: GC-2025 produced by Shimadzu Corporation
Viscometer: DV-I Prime digital viscometer produced by Brookfield
GPC: HLC-8320GPC produced by Tosoh Corporation Example 1

As a perfluorodioxolane compound-containing composition, 20.0 g of perfluoro(2-methylene-4-methyl-1,3-dioxolane) (GC areal ratio=99.90%; 2-hydro-perfluoro(2,4-dimethyl-1,3-dioxolane) GC areal ratio=0.05%) was placed in a 30 mL nitrogen-filled polyethylene sample bottle, and 0.0020 g (100 ppm by weight) of perfluoro-p-benzoquinone, which is the exemplified compound 3-15 shown above, was then added as a quinone compound. The sample bottle was then shaken at room temperature, and it was confirmed by eye that the perfluoro-p-benzoquinone had completely dissolved. The sample bottle was then stored under shielding of light and filling of nitrogen for 30 days at room temperature. In order to confirm a polymerization inhibition effect, a portion (0.30 g) of the solution was sampled after being stored for 30 days, and then added to 3.0 g of c-$C_5F_7H_3$ (Zeorora H produced by Nippon Zeon Co., Ltd.), which is a poor solvent for poly[perfluoro(2-methylene-4-methyl-1,3-dioxolane)], and it was confirmed that the solution was homogeneous and that a polymer of perfluoro(2-methylene-4-methyl-1,3-dioxolane) had not been generated.

Furthermore, when a portion (1.20 g) of the solution was dried using an evaporator after storage, it was confirmed that no solid residue (polymer) remained. That is, it was confirmed that a polymerization inhibition effect was achieved. In addition, the color of the solution was confirmed by eye after storage, and found to be colorless. That is, it was confirmed that coloration was suppressed.

Comparative Example 1

Tests were carried out using methods similar to those used in Example 1, except that perfluoro-p-benzoquinone was not added. After 30 days, when a portion (0.30 g) of the solution was sampled and added to 3.0 g of c-$C_5F_7H_3$ (Zeorora H produced by Nippon Zeon Co., Ltd.), which is a poor solvent for poly[perfluoro(2-methylene-4-methyl-1,3-dioxolane)], a white precipitate was generated and it was surmised that partial polymerization had progressed during storage. In addition, when a portion (1.18 g) of the solution was dried using an evaporator and then dried under reduced pressure after storage, it was confirmed that 0.014 g (1.2 weight %) of solid residue (polymer) remained.

Example 2 and Comparative Examples 2 to 4

Tests were carried out using methods similar to those used in Example 1, except that a compound shown in Table 1 was present as a stabilizer at a concentration shown in Table 1 in the perfluoro(2-methylene-4-methyl-1,3-dioxolane). The results are shown in Table 1.

TABLE 1

| | Stabilizer | Concentration (ppm by weight) | Solubility*[2] | Polymerization inhibition*[3] | Color of solution after storage |
|---|---|---|---|---|---|
| Example 1 | Exemplified compound 3-15 | 100 | ○ | ○ | Colorless |
| Example 2 | Exemplified compound 3-1 | 100 | ○ | ○ | Pale yellow |
| Comparative Example 1 | None | — | — | x | Colorless |
| Comparative Example 2 | BHT*[1] | 100 | ○ | x | Colorless |
| Comparative Example 3 | p-methoxyphenol | 100 | ○ | x | Colorless |
| Comparative Example 4 | DL-α-tocopherol | 100 | ○ | ○ | Orange |

*[1] 3,5-di-tert-butyl-4-hydroxytoluene
*[2] ○ Stabilizer completely dissolved, x Insoluble residue
*[3] ○ No polymer precipitation when c-$C_5F_7H_3$ added, x Polymer precipitation From the results shown in Table 1, it can be confirmed that in Example 1 and Example 2, coloration of the composition after storage was suppressed and an excellent polymerization suppression effect was achieved.

In contrast, a polymerization suppression effect could not be confirmed in Comparative Example 2 and Comparative Example 3, in which a phenyl compound known in the past as a stabilizer was present, and significant coloration occurred after storage in Comparative Example 4, in which DL-α-tocopherol was added.

Examples 3 to 11 and Comparative Example 5

As a perfluoro(2-methylene-4-methyl-1,3-dioxolane)-containing composition, 30.0 g of perfluoro(2-methylene-4-methyl-1,3-dioxolane) (GC areal ratio=99.90%; 2-hydroperfluoro(2,4-dimethyl-1,3-dioxolane) GC areal ratio=0.05%, viscosity=0.6 mPa·s) was placed in a 30 mL nitrogen-filled polyethylene sample bottle. Next, samples were prepared by adding stabilizers shown in Table 2 as quinone compounds at concentrations shown in Table 2. In Examples 3, 4 and 6 to 11 and Comparative Example 5, the sample bottle was stored under shielding of light and filling of nitrogen for 30 days at room temperature. After being stored for 30 days, the viscosity of the composition was measured using a viscometer (at a measurement temperature of 20° C.) in order to confirm the progress of polymerization of the contents of the sample bottle. In Example 5, the sample bottle was stored under shielding of light and filling of nitrogen at a temperature of −20° C. for 3 months, and the viscosity was then measured using a viscometer (at a measurement temperature of 20° C.) in order to confirm the progress of polymerization of the contents of the sample bottle after storage for 3 months.

In addition, in Examples 3 to 11 and Comparative Example 5, the color of the solution after storage was confirmed by eye for a sample to which 500 ppm by weight of the stabilizer had been added.

The results are shown in Table 2.

TABLE 2

| | Stabilizer | Viscosity (mPa · s) | | | | Color of solution after storage |
|---|---|---|---|---|---|---|
| | | 10 ppm by weight | 30 ppm by weight | 100 ppm by weight | 500 ppm by weight | |
| Example 3 | Exemplified compound 3-15 | 0.6 | 0.6 | 0.6 | 0.6 | Colorless |
| Example 4 | Exemplified compound 3-1 | 0.6 | 0.6 | 0.6 | 0.6 | Pale yellow |
| Comparative Example 5 | DL-α-tocopherol | 3.4 | 2.5 | 0.6 | 0.6 | Orange |
| Example 5 | Exemplified compound 3-15 | 0.6 | 0.6 | 0.6 | 0.6 | Colorless |
| Example 6 | Exemplified compound 3-9 | 0.6 | 0.6 | 0.6 | 0.6 | Pale yellow |
| Example 7 | Exemplified compound 3-10 | 0.6 | 0.6 | 0.6 | 0.6 | Pale yellow |
| Example 8 | Exemplified compound 3-17 | 0.6 | 0.6 | 0.6 | 0.6 | Pale yellow |
| Example 9 | Exemplified compound 4-1 | 0.6 | 0.6 | 0.6 | 0.6 | Pale orange |
| Example 10 | Exemplified compound 4-10 | 0.6 | 0.6 | 0.6 | 0.6 | Pale yellow |
| Example 11 | Exemplified compound 4-19 | 0.6 | 0.6 | 0.6 | 0.6 | Colorless |

(For samples whose viscosity had increased, when a portion (1 g) of the solution was dried using an evaporator and then dried under reduced pressure, it was confirmed that a solid residue remained. For samples whose viscosity had not increased, no solid residue was confirmed even when the sample was dried and then dried under reduced pressure.)

From the results shown in Table 2, it can be confirmed that in Examples 3 to 11, an excellent stabilizing effect (polymerization suppression effect) was achieved even at a low stabilizer concentration.

In contrast, in Comparative Example 5, in which DL-α-tocopherol was present as a stabilizer, the viscosity of the solution increased at a concentration of less than 100 ppm by weight, which suggests that polymerization had progressed.

In addition, from the results shown in Table 2, it can be confirmed that in Examples 3 to 11, in which a quinone compound denoted by general formula (3) or general formula (4) was present, coloration was better suppressed than in Comparative Example 5, in which DL-α-tocopherol was present. Of these, it can be confirmed that a coloration suppression effect was greater in Example 5 and Example 11, in which a perfluoro compound was present as the quinone compound denoted by general formula (3) or general formula (4).

Examples 12 and 13

As a perfluoro(2-methylene-4-methyl-1,3-dioxolane)-containing composition, 25.0 g of perfluoro(2-methylene-4-methyl-1,3-dioxolane) (GC areal ratio=99.27%; 2-hydro-perfluoro(2,4-dimethyl-1,3-dioxolane) GC areal ratio=0.46%, viscosity=0.6 mPa·s) was placed in a 30 mL nitrogen-filled polyethylene sample bottle. Next, samples were prepared by adding perfluoro-p-benzoquinone, which is exemplified compound 3-15, as a quinone compound at a concentration shown in Table 3. In Example 12, the sample bottle was stored under shielding of light and filling of nitrogen for 90 days at room temperature. After being stored for 90 days, the viscosity of the composition was measured using a viscometer (at a measurement temperature of 20° C.) in order to confirm the progress of polymerization of the contents of the sample bottle. In addition, the color of the solution after storage was confirmed by eye for all of the samples. In Example 13, the sample bottle was stored under shielding of light and filling of nitrogen at a temperature of −20° C. for 6 months, and the viscosity of the composition was then measured using a viscometer (at a measurement temperature of 20° C.) in order to confirm the progress of polymerization of the contents of the sample bottle after 6 months. In addition, the color of the solution after storage was confirmed by eye for all of the samples. The results are shown in Table 3.

TABLE 3

| | | Viscosity (mPa · s) | | | | |
|---|---|---|---|---|---|---|
| | Stabilizer | 0.1 ppm by weight | 0.3 ppm by weight | 1.0 ppm by weight | 3.0 ppm by weight | Color of solution after storage |
| Example 12 | Exemplified compound 3-15 | 0.8 | 0.7 | 0.6 | 0.6 | All colorless |
| Example 13 | Exemplified compound 3-15 | 0.6 | 0.6 | 0.6 | 0.6 | All colorless |

(For samples whose viscosity had increased, when a portion (1 g) of the solution was dried using an evaporator and then dried under reduced pressure, it was confirmed that a solid residue remained. For samples whose viscosity had not increased, no solid residue was confirmed even when the sample was dried and then dried under reduced pressure.)

From the results shown in Table 3, it can be confirmed that in Example 12 and Example 13, an excellent stabilizing effect (polymerization suppression effect) was achieved even at a low stabilizer concentration.

Example 14, Comparative Example 6

10 g of perfluoro(2-methylene-4-methyl-1,3-dioxolane) (GC areal ratio=99.90%; 2-hydro-perfluoro(2,4-dimethyl-1,3-dioxolane) GC areal ratio=0.05%) containing 10 ppm by weight of perfluoro-p-benzoquinone, which is Exemplified Compound 3-15, as a quinone compound, 40 g of c-C5F7H3 (Zeorora H produced by Nippon Zeon Co., Ltd.) as a polymerization solvent and 0.086 g of perfluorobenzoyl peroxide as a polymerization initiator were placed in a glass tube (capacity 100 mL), and a reaction was carried out at 55° C. for 24 hours. After the reaction, a generated precipitate was filtered to obtain poly[perfluoro(2-methylene-4-methyl-1,3-dioxolane)].

The yield and molecular weight (measured using a GPC method) of the obtained polymer were compared with Comparative Example 6, in which a similar procedure was carried out without adding a stabilizer. The results are shown in Table 4.

TABLE 4

| | Stabilizer | Stabilizer concentration (ppm by weight) | Yield (g) | Molecular weight ($\times 10^{-4}$) |
|---|---|---|---|---|
| Example 14 | Exemplified compound 3-15 | 10 | 7 | 14.5 |
| Comparative Example 6 | None | None | 7 | 14.3 |

From the results shown in Table 4, it can be confirmed that in Example 14, it was not necessary to carry out a stabilizer removal operation such as purification by distillation prior to polymerization, and a polymerization reaction can progress in the same way as in a case where a stabilizer is not contained.

According to one aspect of the present invention, it is now possible to provide a perfluorodioxolane compound-containing composition that is unlikely to undergo changes in quality, such as polymerization reactions and coloration, during storage. A thus stabilized perfluorodioxolane compound-containing composition can be used as a raw material for synthesizing resins for gas separation membranes and transparent resins for optical fibers.

The invention claimed is:

1. A method of stabilizing a perfluorodioxolane, comprising:
    having a quinone present in a composition including the perfluorodioxolane,
    wherein the perfluorodioxolane comprises at least one selected from the group consisting of:

a compound of formula (1),

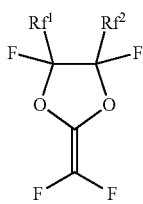

(1)

wherein $Rf^1$ and $Rf^2$ each independently denote a fluorine atom or a perfluoroalkyl group having 1 to 6 carbon atoms, an ether bond is optionally present in a carbon-carbon bond in the perfluoroalkyl group, and the $Rf^1$ and $Rf^2$ may optionally bond to each other to form a ring; and a compound of formula (2),

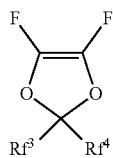

(2)

wherein $Rf^3$ and $Rf^4$ each independently denote a fluorine atom or a perfluoroalkyl group having 1 to 6 carbon atoms, and an ether bond is optionally present in a carbon-carbon bond in the perfluoroalkyl group; and the quinone comprises at least one selected from the group consisting of:

a compound of formula (3),

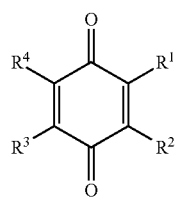

(3)

wherein $R^1$ to $R^4$ each independently denote a hydrogen atom, a fluorine atom or a chlorine atom; and a compound of formula (4),

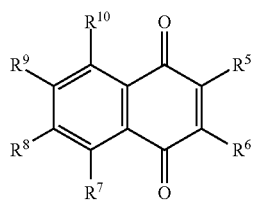

(4)

wherein $R^5$ to $R^{10}$ each independently denote a hydrogen atom, a fluorine atom or a chlorine atom.

2. The method according to claim 1, wherein at least one of the $R^1$ to $R^4$ in the general formula (3) is a fluorine atom.

3. The method according to claim 1, wherein the quinone comprises the compound of formula (3).

4. The method according to claim 1, wherein the quinone comprises perfluoro-p-benzoquinone.

5. The method according to claim 1, wherein at least one of the $R^5$ to $R^{10}$ in the formula (4) is a fluorine atom.

6. The method according to claim 1, wherein the quinone is present at a weight ratio of 0.1 to 500 ppm relative to the perfluorodioxolane.

7. The method according to claim 6, further comprising:

holding the composition, in which the quinone is present, in a container including a gas phase part including an inert gas.

8. The method according to claim 1, further comprising:

holding the composition, in which the quinone is present, at a temperature of 0° C. or lower.

9. A composition, comprising:

a perfluorodioxolane; and a quinone, wherein the perfluorodioxolane comprises at least one selected from the group consisting of:

a compound of formula (1),

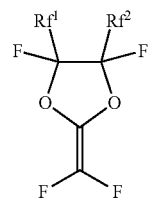

(1)

wherein $Rf^1$ and $Rf^2$ each independently denote a fluorine atom or a perfluoroalkyl group having 1 to 6 carbon atoms, an ether bond is optionally present in a carbon-carbon bond in the perfluoroalkyl group, and the $Rf^1$ and $Rf^2$ may optionally bond to each other in a ring; and a compound of formula (2),

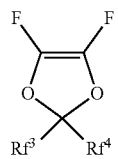

(2)

wherein $Rf^3$ and $Rf^4$ each independently denote a fluorine atom or a perfluoroalkyl group having 1 to 6 carbon atoms, and an ether bond is optionally present in a carbon-carbon bond in the perfluoroalkyl group; and wherein the quinone comprises at least one selected from the group consisting of:

a compound of formula (3),

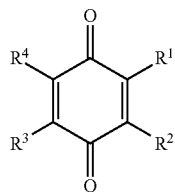

(3)

wherein $R^1$ to $R^4$ each independently denote a hydrogen atom, a fluorine atom or a chlorine atom; and a compound of formula (4),

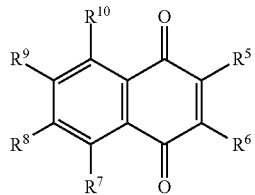

(4)

wherein $R^5$ to $R^{10}$ each independently denote a hydrogen atom, a fluorine atom or a chlorine atom.

10. The composition according to claim 9, wherein the quinone is present at a weight ratio of 0.1 to 500 ppm relative to the perfluorodioxolane.

11. The composition according to claim 9, wherein at least one of the $R^1$ to $R^4$ in the formula (3) is a fluorine atom.

12. The composition according to claim 9, wherein the quinone comprises the compound of formula (3).

13. The composition according to claim 9, wherein the quinone comprises perfluoro-p-benzoquinone.

14. The composition according to claim 9, wherein at least one of the $R^5$ to $R^{10}$ in the formula (4) is a fluorine atom.

15. A method producing a perfluorodioxolane polymer, comprising:
adding a polymerization initiator to the composition of claim 9, such that the perfluorodioxolane is polymerized.

16. The composition according to claim 9, further comprising:
a perfluorodioxolane polymer at a content of 1.0 weight % or less after the composition is stored under filling of nitrogen for at least one week.

17. A method producing a perfluorodioxolane polymer, comprising:
adding a polymerization initiator to the composition of claim 16, such that the perfluorodioxolane is polymerized.

18. The method according to claim 2, wherein the quinone comprises perfluoro-p-benzoquinone.

19. The method according to claim 3, wherein the quinone comprises perfluoro-p-benzoquinone.

20. The method according to claim 2, wherein at least one of the $R_5$ to $R_{10}$ in the formula (4) is a fluorine atom.

* * * * *